United States Patent [19]

Gouesbet

[11] 4,373,807

[45] Feb. 15, 1983

[54] METHOD AND APPARATUS FOR THE SIMULTANEOUS MEASUREMENT OF DATA, INCLUDING VELOCITY, RELATING TO SUBMICRONIC PARTICLES IN A STATE OF FLOW IN A FLUID

[75] Inventor: Gérard Gouesbet, Mont Saint Aignan, France

[73] Assignee: Agence Nationale de Valorisation de la Recherche (ANVAR), Neuilly sur Seine, France

[21] Appl. No.: 124,545

[22] Filed: Feb. 25, 1980

[30] Foreign Application Priority Data

Feb. 27, 1979 [FR] France .............................. 79 05089

[51] Int. Cl.³ ........................ G01P 3/36; G01N 15/02
[52] U.S. Cl. .................................. 356/28.5; 356/335
[58] Field of Search .............................. 356/28.5, 335

[56] References Cited

U.S. PATENT DOCUMENTS 3,675,029 7/1972 Iten et al. ........................... 356/28.5
3,860,342 1/1975 Orloff et al. ...................... 356/28.5

FOREIGN PATENT DOCUMENTS 1592220 6/1970 France ............................... 356/28.5

OTHER PUBLICATIONS

T. Sato et al., Applied Optics, vol. 17, No. 2, Jan. 1978, pp. 230–234.
N. S. Hong et al., J. of Physics D, vol. 9, No. 13, Sep. 1976, p. 1839.
B. S. Rinkevichyus et al., Radio Engineering and Electronic Physics, vol. 18, No. 7, Jul. 1973, p. 1000.
H. Oertel et al., Applied Optics, vol. 17, No. 22, Nov. 1978, p. 3535.
F. K. Owen, Agard Conf. Proc., No. 193, Saint-Louis, France, 3-5 May, 1976, pp. 27–31.
P. Buchhave, Optics and Laser Tech., Feb. 1975, vol. 7, No. 1, pp. 11–16.
I. Chabay et al., Dimensions/NBS, Dec. 1978, pp. 16–17.
D. A. Ross et al., J. of Colloid and Interface Science, vol. 64, No. 3, May 1978.

*Primary Examiner*—S. C. Buczinski
*Attorney, Agent, or Firm*—Burns, Doane, Swecker & Mathis

[57] ABSTRACT

The same assembly is used to first record the homodyne spectrum from the light diffused from a single beam $FL_2$, with a mask $D_1$ masking the beam $FL_1$. On the passage of a critical frequency $f_c$, mask $D_1$ is removed, the aperture of a diaphragm $D_2$ is reduced, and the heterodyne spectrum produced by $FL_1$ and $FL_2$ is recorded as received by a photomultiplier PM and a spectrum analyzer AS.

12 Claims, 4 Drawing Figures

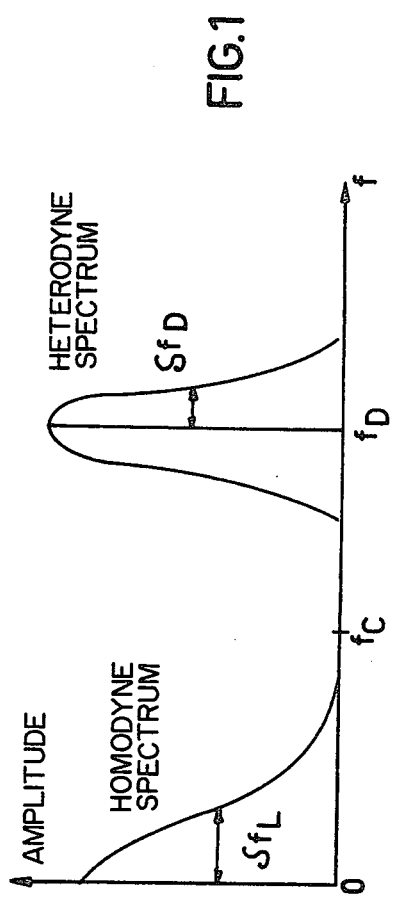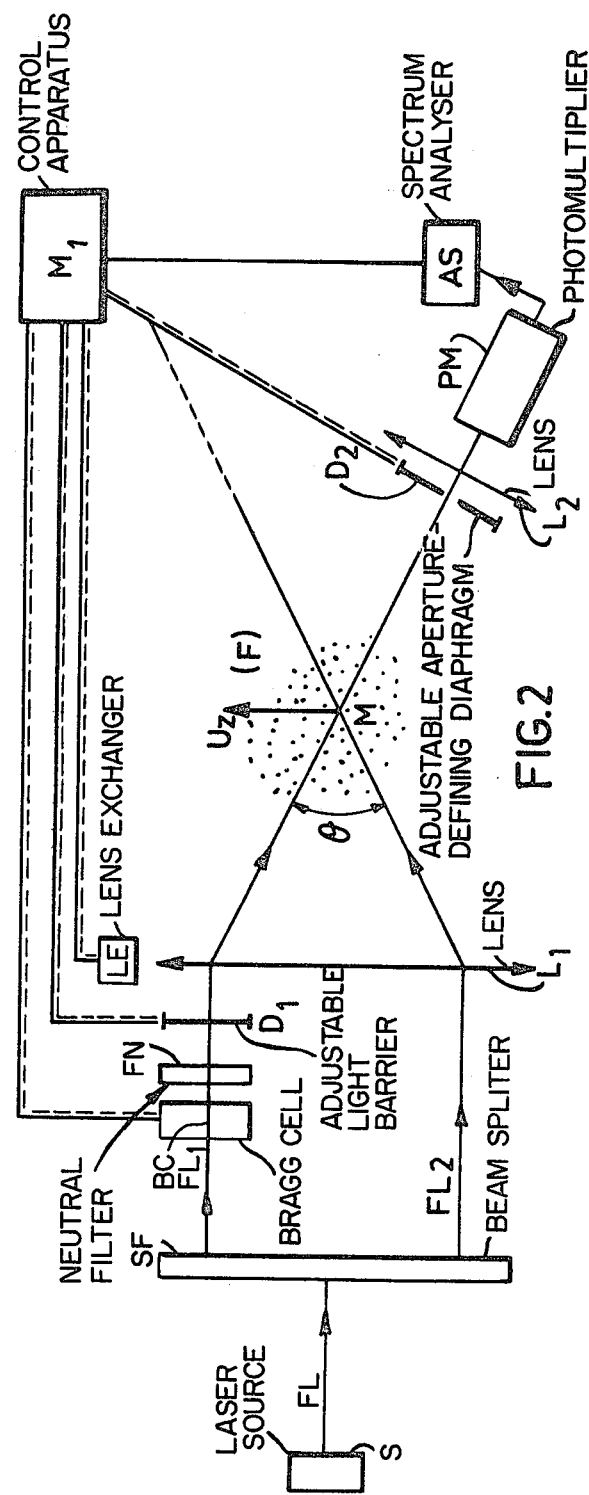

METHOD AND APPARATUS FOR THE SIMULTANEOUS MEASUREMENT OF DATA, INCLUDING VELOCITY, RELATING TO SUBMICRONIC PARTICLES IN A STATE OF FLOW IN A FLUID

FIELD OF THE INVENTION

The invention relates to a method and apparatus permitting the simultaneous measurement of velocities, velocity fluctuations, diameters and all other data of submicronic particles in a state of flow in a fluid medium. As used in this application the term "submicronic" refers to particles which have dimensions roughly equal to or smaller than one micron.

The invention also relates to the application of this method and apparatus to a great variety of fields, such as environmental science (monitoring of factory chimneys), mechanical plants (control of radiation furnaces, combustion engines and others), and medicine. By introducing particles of known size into a medium, the invention conversely permits measurement of the temperature of the medium.

BACKGROUND OF THE INVENTION

Devices are already known which permit the individual measurement of velocities, velocity fluctuations, or diameters of submicronic particles. However no apparatus known at present permits the simultaneous determination of the three above-mentioned parameters for a given fluid.

An example of a prior art device which uses laser techniques for measurements of sundry dynamic properties of fluids is disclosed in the article by John C. Angus et al. "Motion Measurement by Laser Doppler Techniques", in Industrial and Engineering Chemistry, Vol. 61, No. 2, Feb. 1969, p. 8 et seq.

The proposed apparatus disclosed by Angus et al is designed to detect a given spectrum, but its design makes it unsuitable for the simultaneous recording of a homodyne spectrum and a heterodyne spectrum.

In order to arrive at an experimental determination of the three required quantities (velocities, velocity fluctuations and particle diameters), it is necessary at present to use two devices, the first being used to measure velocities and velocity fluctuations of the fluid, the second used to determine the diameters of the particles contained in the said fluid.

The fact that according to the previous technique it is necessary to use two devices has its disadvantages. On the one hand it means that two measurements have to be made which are separated by a considerable time interval, i.e., one velocity and velocity fluctuation is determined at a time t and a particle diameter is determined at a time $t_1$. But between these two measurement times the conditions of the experiment may have varied and there is never any certainty whether the measured velocity corresponds to the diameter determined at a later time. Furthermore, the fact that two measurements have to be made necessitates an analysis time which is much too long, and may be as much as one day. The above-mentioned disadvantages can be avoided by means of the invention. In fact it permits the simultaneous measurement of velocities, velocity fluctuations and particles diameters of the fluid in question. Consequently the three required quantities can be determined at the same time t.

Furthermore, the invention permits a reduction in operation time, allowing a spectrum to be obtained within a period of a few minutes (and even a few seconds). The spectrum which is thus obtained can then be used to obtain the actual measurement of the three factors required.

The invention relates to a method and apparatus for the simultaneous measurement of velocities, velocity fluctuations, diameters and other data concerning submicronic particles in a state of flow in a fluid wherein two parallel beams of coherent light are produced from a single laser beam, the beams are focused in the fluid zone to be measured, and the light issuing from the zone is spectrally analysed. According to the present invention, a homodyne spectrum is first recorded by a frequency sweep over a first frequency range of the diffused light received from one of the parallel beams at a first detection angle, and a heterodyne spectrum is then recorded by continuing the frequency sweep over a second frequency range of the diffused light received from the one beam and the light received from the other, previously blocked beam at a second detection angle. A frequency $f_c$ is defined, termed the critical frequency, higher than the highest frequency of the homodyne spectrum, which is used as a control parameter to control the emission and reception of the coherent light beams.

The data of the two spectra is then processed in order to simultaneously determine the values for velocities, velocity fluctuations and particle diameters within the zone in question.

According to the present invention, two beams from the same laser source are focused in a spatial zone encompassing the fluid to be analysed.

A spectrum analyser sweeps the signal produced by photodetector apparatus by pass-bands (frequency sweep) within periods exceeding 0.1 ms by several orders of magnitude. According to an essential characteristic of the invention, the analyser first works on one beam and then, from the critical frequency, on the two beams.

The total spectrum recorded contains all the required data: the homodyne spectrum permitting determination of particle diameter, and the heterodyne spectrum permitting determination of the velocities and velocity fluctuations of the particles in the fluid.

These and other features and advantages of the present invention are disclosed in or apparent from the following detailed description of preferred embodiments.

BRIEF DESCRIPTION OF THE DRAWINGS

The preferred embodiments will be described with reference to the accompanying drawings in which FIG. 1 schematically shows the spectrum obtained on the spectrum analyser in accordance with the present invention;

FIG. 2 shows a schematic diagram of a first embodiment of apparatus according to the invention;

DETAILED DESCRIPTION OF PREFERRED EMBODIMENTS

Figure 3:
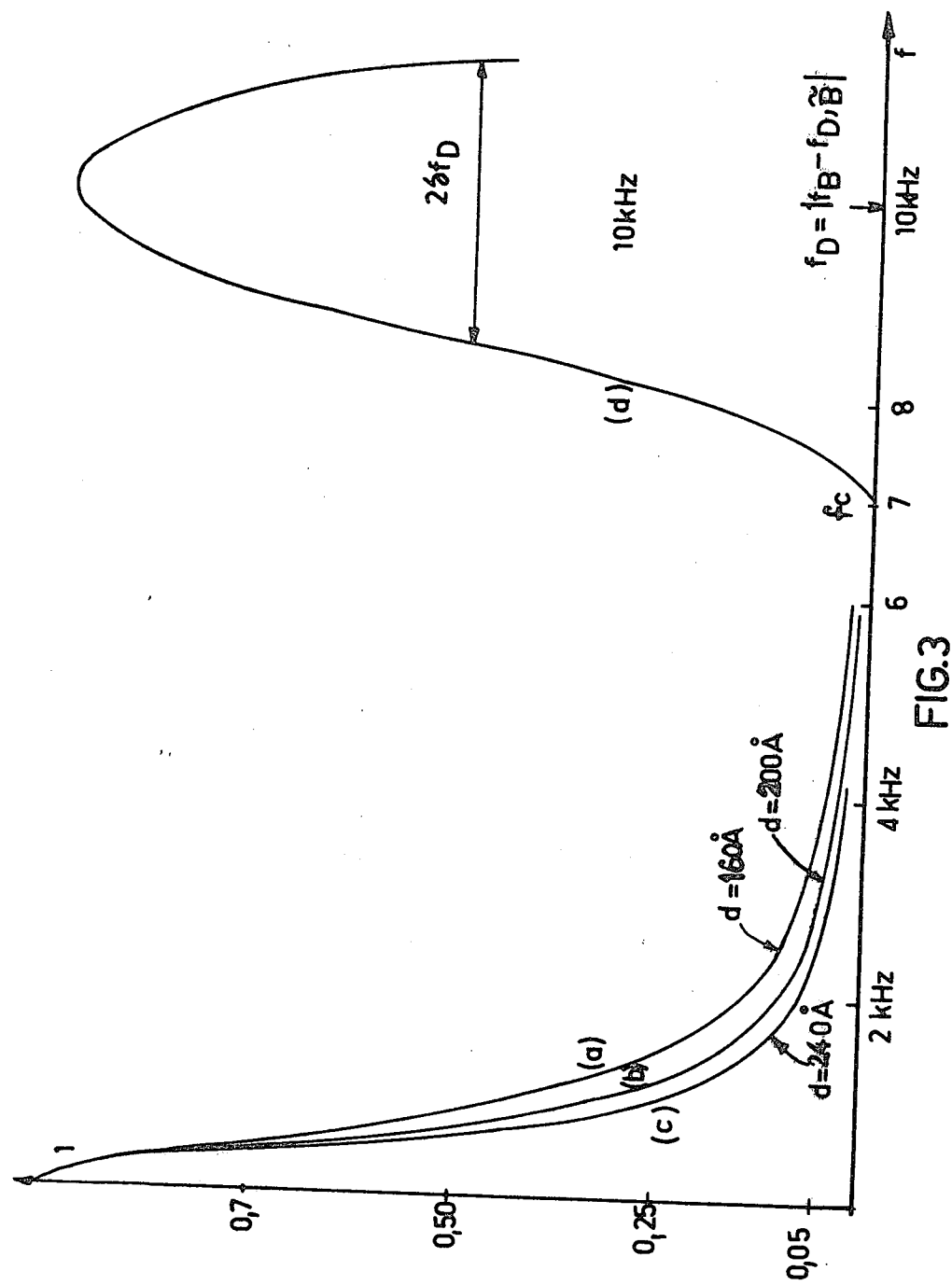
FIG. 3 shows the spectra obtained in an exemplary application of the invention to measurements of a flame.

According to the invention, in order to record the homodyne spectrum, only one laser beam is allowed to pass. The diffused light from this beam is collected by a photomultiplier at a detection angle which is a fairly wide solid angle.

The diffused light is spectrally broadened by one quantity ($\delta f_L$), by Doppler effect, caused by the Brownian motion of a large number of particles present at each instant in the field of resolution. In FIG. 1 the value $\delta f_L$ corresponding to half spectrum height has been marked.

The diffused curve is Lorentzian. (in some known conditions). The smaller the diameter of the particles becomes, the greater the velocity of Brownian motion, and the more the Doppler effect increases and thus $\delta f_L$. Thus $\delta f_L$ is a mesure of d, particle diameter, the particles considered to be monodispersed.

The measurement is made by studying the beating of the diffused beam with itself using a photomultiplier. The spectrum of the signal from the photomultiplier is then written:

$$S = \frac{\alpha D}{(\alpha D)^2 + W^2}$$

where $\alpha$ depends on the characteristics of the optical apparatus.

W is the angular frequency on the spectral analyser and

D is the coefficient of Brownian diffusion of particles given by $$D = k\ T/3\ \mu d$$

where k is the Boltzmann constant
T absolute temperature
$\mu$ viscosity of fluid
d diameter of particles.

Recording of the homodyne spectrum S thus permits measurement of D and of d, if the temperature T is known.

The heterodyne spectrum (using a reference frequency, i.e. that of the first laser beam) is recorded under conditions such that the first laser beam and the light diffused from the second beam reach the photomultiplier at a detection angle which is a small solid angle. The heterodyne spectrum permits measurement of the velocity and of the particle velocity fluctuation.

The diffused light is offset in phase relative to the reference frequency by a frequency $f_{D,\ B}$ called the Doppler frequency, due to the general motion of the particles in the field M, which is identical to the general motion of the fluid for the submicronic particles.

The Doppler shift is given by $$f_{D,\ \widetilde{B}} = \frac{2 f u_z \sin(\theta/2)}{c}$$

where f is the laser frequency,
$u_z$ is the component of fluid velocity in the direction perpendicular to the plane of the fringes formed by beams FL$_1$ and FL$_2$,
c is the velocity of light in the medium and
$\theta$ is the angle between the first and the second laser beam.

The heterodyne spectrum giving $f_{D,\ \widetilde{B}}$, the value of $u_z$ can thus be calculated, which is a measure of the overall velocity of the particles.

According to a supplementary characteristic of the invention, it is often desirable to convert the Doppler frequency $f_{D,\ \widetilde{B}}$ back to the scale of the spectrum analyser.

Since the recording of the spectrum is carried out for several times of 0.1 ms, the spectrum also contains a broadening due to the random motion of the particles under turbulence. (if the flow is turbulent). If the turbulence is Gaussian, there results a Gaussian magnification characterized by a width at half-height $\delta f_D$. The spectrum gives $\delta f_D$ which is a measure of the particle velocity fluctuation.

According to another characteristic of the invention, supplementary apparatus is provided for reducing the magnification $\delta f_D$. For this purpose the optical apparatus can be modified, for example, in response to the critical frequency $f_c$ and/or lens L$_1$ can be changed after recording the homodyne spectrum, as will be illustrated in the following example.

Apparatus in accordance with the present invention for the implementation of the process as described above comprises a laser source, a beam splitter doubling the laser beam into a first and a second laser beam parallel to one another, a neutral filter, a system permitting focussing of the two beams in the zone where the fluid to be analysed is located, a photomultiplier connected to a spectrum analyser, a controllable light barrier (D$_1$) for selectively blocking a first one of the parallel beams (FL$_1$), a diaphragm (D$_2$) with adjustable aperture cooperating with a convergent lens (L$_2$) located in the path of the first beam (FL$_1$) after it has been focussed, and apparatus cooperating with the spectrum analyser to control in response to a critical frequency $f_c$ the operation of the light barrier (D$_1$) and the reduction of the diaphragm aperture (D$_2$). Preferably, the photomultiplier is located at a fixed position in the extended path of the blockable beam (FL$_1$), such that all the measuring operations can be effected without changing the position of the photomultiplier.

The laser source used can be an ionized argon source (supplying for example roughly 1 W power over a line of 514.5 mm), and in particular a laser operating in the mode TEM$_{00}$, although these specifications are in no way exclusive of others.

In order to reduce to a minimum the beating effect between the longitudinal modes of the laser, it is preferable to compensate the optical trajectories of the first and second laser beams in the beam splitter.

The type of beam splitter used is not of critical importance. It can be of known type such as is used in a great number of equivalent optical devices.

The light barrier can consist of a conventional electronically controllable mask, opaque screen or the like.

The angle between the first and second laser beams on leaving the focusing system is between 0° and 90°. The angle selected is a function of the fluid being analysed, i.e. of velocity, velocity fluctuations and particle diameter. This angle $\theta$ can be modified by changing the optical assembly, i.e. a focusing lens.

The incident laser light is diffused by the submicronic particles present in suspension in the fluid located or moving through the measurement zone.

The function of the lens L$_2$ is to combine the field M and the photomultiplier.

When the frequency sweep of the spectrum analyzer passes the frequency $f_c$, a control pulse is generated which causes the control apparatus to change the optical apparatus from a homodyne configuration to a heterodyne configuration, i.e., the light barrier ceases to block the beam $FL_1$ and the aperture of the diaphragm is reduced in order to limit the solid angle of collection of diffused light.

Many methods known in the art can be used to effect these two changes. By way of example, the light barrier can consist of a curtain diaphragm of a commercially available type wherein the curtain movement is controlled electronically in response to a control signal. Similarly, the diaphragm can be a conventional photographic iris diaphragm which is capable of being closed by electronic control in response to a pulse corresponding to frequency $f_c$. It will be appreciated these examples are given purely by way of example.

Preferably a system according to the invention also comprises apparatus for converting the Doppler frequency $f_{D,B}$ back to the scale of the spectrum analyser. This apparatus consists advantageously of a Bragg cell mounted in the path of the first laser beam before the focusing lens. The function of such a cell is in fact to modify the frequency. The conversion apparatus could be for example a commercially available diffraction grating.

In addition, a system according to the invention can also include apparatus for reducing the spectral broadening $\delta f_D$ of the diffused light, in particular apparatus for varying the angle $\theta$ between the focused beams.

The apparatus according to the invention permits the obtention of a homodyne and heterodyne spectrum within a very short time of around 2 to 3 minutes.

After display of the two spectra on the spectrum analyser, the spectra are, for example, photographed and processed, knowing $f_{D,B}$, $\delta f_D$ and $\delta f_L$, and using the above mentioned formulas in order to determine respectively the mean velocity of the fluid as a whole, the overall velocity fluctuation, and the diameter of the particles in suspension in the fluid. Of course, the processing of the information contained in the spectra can be by means other than photographic. Thus the data could be transmitted to a computer linked to the spectrum analyser.

Finally, the invention relates to the utilization of the apparatus according to the invention for the determination of the three above mentioned quantities, based on in situ measurements in furnaces, in flames, in combustion engines, at the outlet factory chimneys, and in all sorts of other applications.

For example it is known that the transfer of heat by radiation in a furnace depends greatly on the presence of soot. The furnace must be controlled in order to have an optimum emission of such soot.

On the other hand, in a combustion engine, the emission of soot must be kept to a minimum. The engine is thus controlled in such a way as to minimize soot emission. The apparatus according to the invention permits determination at each instant of the composition of the fluid moving in a furnace or in a combustion engine. All that is then required is to adjust the plant to obtain the desired soot emission.

This apparatus also finds an application in environmental science where it permits, when mounted on factory chimneys, determination of the emission of soot and other particles, and consequently provide for an adequate cleaning of plant emissions. The specific embodiment hereinafter described clearly shows the value of the apparatus according to the invention for studying a turbulent combustion flame.

The invention can also find an application in medicine, because at present the trend is towards regarding the phenomenon causing cancers as possibly being of submicronic origin.

The invention can also be used in calorimetry. In this case an inverse measurement is made in the sense that particles of known size are introduced into a medium temperature of which is to be determined, spectrum recorded is then analyzed to measure the temperature T.

By reference to FIGS. 1 and 2 it can be seen that a first specific embodiment of the invention makes use, as is known, of a laser source S emitting a beam FL which beam is split into two substantially parallel beams $FL_1$ and $FL_2$ by a beam separator or splitter SF. A neutral filter FN and a controllable light barrier $D_1$ are disposed in the optical path of beam $FL_1$ in front of a focusing lens $L_1$. Advantageously, a conventional automatic lens exchanger LE is also provided which is responsive to a control signal for changing lens $L_1$. The two beams $FL_1$ (with light barrier $D_1$ not blocking the light path) and $FL_2$ converge in a spatial field or zone M, after passing through lens $L_1$, in order to form an interference field. An embodiment of lens $L_1$ is used which has a focal length such that beams $FL_1$ and $FL_2$ converge exactly in the field M where the fluid (F) to be analyzed is flowing. The characteristics of the spatial field M depend on the laser incident light (wavelength, diameter of beams) and on the angle $\theta$ formed between the beams $FL_1$ and $FL_2$ at the outlet of the focusing lens $L_1$. Field M has for example a length of about $300\mu$ and a width of about $50\mu$. In field M, the overall speed of the particles in direction perpendicular to the plane of the fringes formed at M by beams $FL_1$ and $FL_2$ is indicated by $u_z$. The incident laser light is diffused by the submicronic particles in this field M, in suspension in the fluid (F). It is assumed that the number of particles present in M is sufficiently great (this is for example the case of particles of soot in a flame). In the optical path of $FL_1$, after passage through field M and in front a photomultiplier PM, a diaphragm $D_2$ is mounted, of adjustable aperture, together with a lens $L_2$. The photomultiplier PM thus receives the beam $FL_1$ (light barrier $D_1$ removed) and the light diffused by the particles present in M, from beam $FL_2$. Photomultiplier PM is connected to a spectrum analyser AS which produces the spectral recording. According to an essential characteristic of the invention, conventional, preferably electronic, control apparatus $M_1$, controlled by spectrum analyser AS, is provided for controlling diaphragm $D_2$, lens exchanger LE and barrier $D_1$. The function of these means $M_1$ and its operating mode are set out below with reference to FIGS. 1 and 2.

Spectrum analyzer AS is configured to conduct a frequency sweep analysis of the output of photomultiplier PM over a first frequency range in order to record first the homodyne spectrum. In this case light barrier $D_1$ is actuated to block beam $FL_1$ so that it cannot pass to zone M. The photomultiplier PM thus receives only the light diffused by beam $FL_2$. Given that the diffused flux is weak, diaphragm $D_2$ is sufficiently opened so that the diffused light is collected, or detected, by photomultiplier PM at a large solid angle. After the homodyne spectrum is recorded the critical frequency $f_c$ is reached, the value of which is determined for example by preliminary experiments. The spectrum analyser AS then emits a pulse to control apparatus M₁ which actuates light barrier D₁ to a non-blocking state and diaphragm D₂ to reduce the aperture thereof such that both light beams FL₁ and FL₂ pass through zone M and photo-multiplier PM receives beam FL₁ and the beam diffused by the particles contained in space M from beam FL₂ at a small solid angle which allows only a very narrow beam to pass. The frequency sweep is continued and the heterodyne spectrum recorded.

FIG. 1 shows the final spectrum obtained on the spectrum analyser. This spectrum supplies $\delta f_L$, which permits calculation of the diameter of the particles, and $f_{D,B}$ and $\delta f_D$, which permit determination of velocities and velocity fluctuations of the particles as a whole. $\delta f_D \approx \delta f_L$ can be obtained by adjusting the geometry of the optical focusing device and its orientation in relation to the mean velocity vector. $f_{D,B} \approx \delta f_L$, can be obtained by adding a Bragg cell BC in the path of the first laser beam, as shown in FIG. 2, which shifts the frequency of beam FL₁ by a quantity $f_B$ of such that the beat frequency becomes $f_D = |f_B - f_{D,\bar{B}}|$ where $f_{D,\bar{B}}$ is the Doppler frequency in the absence of a Bragg cell. As will be appreciated by those of ordinary skill in the art, Bragg cell BC is provided, as shown in FIG. 2, with an input control signal, as is conventional, to control the degree of frequency shift produced by the Bragg cell.

The description now continues with reference to an exemplary application of the apparatus according to the invention in which the soot composition of a turbulent flame is studied.

EXAMPLE

In this example, measurements are made on a turbulent flame (F) such as is emitted by a burner, using the embodiment schematically shown in FIG. 2. Flame (F) contains soot particles and has the following characteristics:

Absolute temperature T = 1500° K.
Dynamic viscosity $\mu = 0.05 \cdot 10^{-3}$ kg/m.s
Mean velocity $\bar{u} = 50$ cm/s
Velocity fluctuations $\delta u/u = 8\%$ ($\delta u$: quadratic shift of the probability density of velocities, assumed to be Gaussian).
Diameter of soot particles d = 200 Å.

The optical assembly is characterized by the angle $\theta$ (see FIG. 2) and the angle $\phi$ between the direction of mean velocity $\bar{u}$ and the plane of the two beams FL₁ and FL₂. We thus have $\phi = (\vec{u}, \vec{u}_z)$, i.e. separation between the beams $\phi$ is the angle between vectors $\mu$ and $\mu_z$.

1. Homodyne spectrum

As mentioned above, the spectrum is expressed:

$$S = \frac{\alpha D}{(\alpha D)^2 + W^2} \quad (1)$$

The spectrum normalized at 1 for W=0 is thus expressed:

$$S_o = \frac{1}{1 + \left(\frac{W}{\alpha D}\right)^2} = \frac{1}{1 + \left(\frac{\pi f}{K^2 D}\right)^2} \quad (2)$$

with $K = \frac{4\pi}{\lambda} \sin\left(\frac{\theta}{2}\right)$

The width at half-height $\delta f_L$ is thus expressed by:

$$\delta f_L = \frac{DK^2}{\pi} \quad 16\pi \frac{\sin^2 \theta/2}{\lambda^2} \cdot \frac{kT}{3\pi \mu d}$$

In the example selected, the apparatus is configured such that $f_L = 0.5$ m, where $f_L$ is the focal length of lens L₁;

$d_L = 4$ cm, where $d_L$ is the separation between beams FL₁ and FL₂;

and thus:

$$\sin(\theta/2) = \frac{d_L/2}{\sqrt{f_L^2 + (d_L/2)^2}} = 0.03997 \sim 0.04.$$

For an ionized argon laser producing a green line ($\lambda = 5145$ Å) we find:

$D = kT/3\pi\mu d = 2.2 \cdot 10^{-9}$ SI;

and thus $\delta f_L = 670$ Hz.

It will be noted that if d = 160 Å or 240 Å, we have respectively $\delta f_L = 830$ and 560 Hz.

It should be noted also that So can also be expressed:

$$S_o = \frac{1}{1 + \left(\frac{f}{\delta f_L}\right)^2}$$

FIG. 3 contains three homodyne spectra (a), (b), (c) corresponding respectively to the three diameters considered: d = 160 Å, d = 200 Å and d = 240 Å. The amplitudes are plotted on the ordinate axis, in normalized units. The frequencies f are plotted on the abscissa axis.

Once the homodyne spectrum is recorded, the invention permits access to any data that it contains, i.e. the mean diameter of the particles as well as possibly the distribution of the diameters in a polydispersed system.

2. Heterodyne Spectrum $f_{D,\bar{B}}$ designates the Doppler frequency in the absence of a Bragg cell. The Doppler frequency with a Bragg cell mounted on the FL₁ beam is then equal to:

$f_D = |f_B - f_{D,\bar{B}}|$.

The Gaussian broadening is:

$$\delta f_D = \delta f_{D,\tilde{B}} = \delta \left[\frac{2 u_z \sin \theta/2}{\lambda}\right] = \frac{2 \sin(\theta/2) \delta u_z}{\lambda}$$

Furthermore, $\delta u_z = \cos \phi \cdot \delta u$
Therefore:

$$\delta f_D = \frac{2}{\lambda} \cos \alpha \sin(\theta/2) \cdot \delta u = 6220 \cos \alpha.$$

We select cos $\phi$ in order to obtain $\delta f_D \sim \delta f_L$, i.e. cos $\phi = 0.2$ ($\phi = 78.5°$). We therefore have:

$\delta f_D = 1244$ Hz.

We have $$f_{D,\tilde{B}} = \frac{2u_z \sin \theta/2}{\lambda} = 15.55 \text{ kHz,}$$

i.e. $f_B = 5.55$ kHz, which gives $f_D = 10$ kHz.

The corresponding heterodyne spectrum is plotted as curve (d) on FIG. 3.

In this case the critical frequency $f_c$ has been set at 7 kHz.

In the above example, the characteristics of the fluid to be studied (in this case a flame containing soot particles) is first determined, e.g., by preliminary experiments. As a function of these known characteristics, $\sin \theta/2$ is then selected in order to obtain a $\delta f_L$ of the desired order of magnitude, $\cos \phi$ is selected in order to bring $\delta f_D$ to a value of around $\delta f_L$, and $f_B$ is selected in order to bring $f_{D,\tilde{B}}$ to the value $f_D$ as desired.

The above considerations show that it is possible—and often necessary—to adjust the parameters of the electronic and optical assembly to the characteristics of the particles to be measured.

It will be noted however that the presence of a Bragg cell permitting continuous adjustment of frequencies is in no way obligatory.

Commercially available Bragg cells produce shifts with certain preset values. It may then be possible to select $\cos \phi$ in order to optimise $u_z = (\cos)$, and thus to obtain a value of $f_{D,\tilde{B}}$ which is close to a frequency $f_B$ produced by the Bragg cell. But in this case it is no longer possible to have a separate optimisation of $\delta f_D$. On the other hand, it is possible to use diffraction gratings rather than Bragg cells in order to have a continuous shift available. In accordance with one aspect of the invention, in order to optimise the heterodyne and homodyne spectra separately, apparatus permitting the production of an angle $\theta$ between the focused beams which differs for the construction of the two spectra is provided which is actuated by control apparatus $M_1$ in response to the critical frequency $f_c$. In one embodiment, the apparatus for varying the angle $\theta$ can include lens exchanger LE or the like for changing the lens $L_1$ on passage of critical frequency $f_c$.

It will be appreciated from the foregoing that numerous versions of the assembly can be provided without departing from the scope of the present invention.

The invention permits the retrieval of all data contained in the experimental spectrum. In particular, the measurement of particle concentrations can be made by analysis of the spectral amplitude.

The above mentioned formula (1) can be written more precisely in the form of a power spectrum:

$$S'(W) = CN^2E^2 \frac{2DK^2}{(2DK^2)^2 + W^2} \qquad (1')$$

where

C is a constant;

N is the number of particles in the field of measurement;

E is the luminous power collected corresponding to the diffusion of light by one particle; and K and D are defined as above.

The recording of a spectrum for a specimen solution (of known characteristics) permits, by amplitude comparison, the measurement of N. For this purpose, a spectrum of light diffused by a sample solution is recorded, and then the aerosol spectrum is studied. The ratio of the amplitudes of these two spectra contains the information about the number of particles per unit of volume (and thus of the concentration by mass) of the aerosol.

Figure 4:
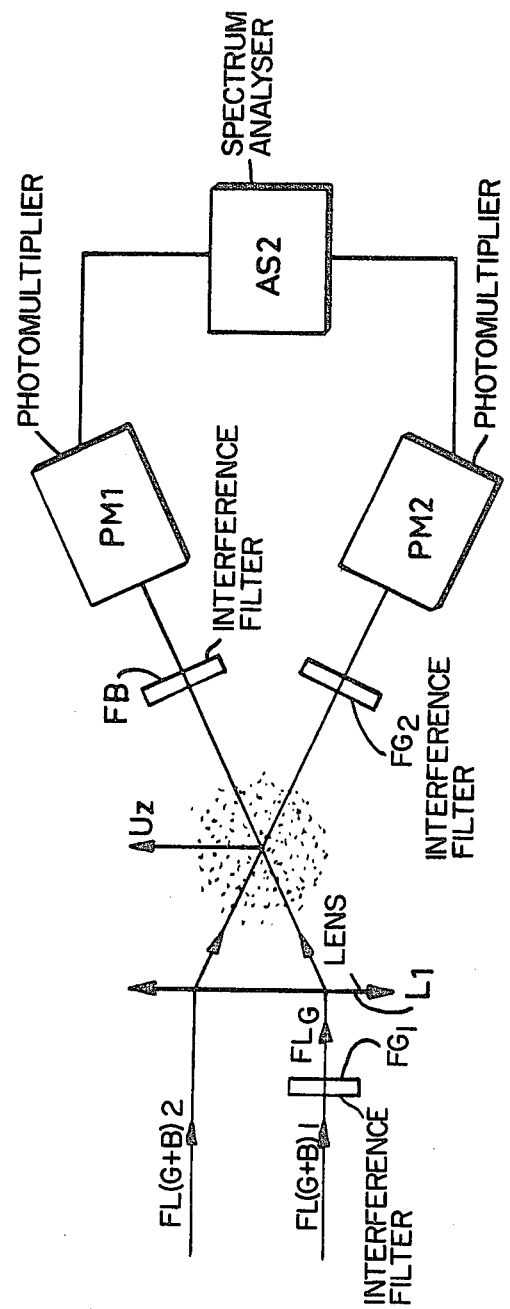
FIG. 4 shows a schematic diagram of a second embodiment of apparatus according to the invention.

Referring to FIG. 4, an embodiment of the present invention will now be described which uses a multi-line laser and allows the measurements to be made totally simultaneously.

Using for example, the blue and green rays, which are the colours most often used for lasers of ionised argon type, and using a set of interference filters, it is possible to simultaneously record the homodyne and heterodyne spectra.

The ionized argon laser source (not shown) supplies two laser beams $FL_{(G+B)1}$ and $FL_{(G+B)2}$ assumed to contain for convenience sake one blue and one green ray. An interference filter $FG_1$ is disposed in the path of beam $FL_{(G+B)1}$, either in front of lens $L_1$, as shown, or after lens $L_1$. The filter $FG_1$ allows only green light to pass, and thus converts beam $FL_{(G+B)1}$ to a beam $FL_G$. There are two photomultipliers PM1 and PM2 which are located in the extended paths of beams $F_G$ and $F_{(G+B)2}$, respectively. Filters FB and $FG_2$ are disposed in front of photomultipliers PM1 and PM2, respectively, and allow only blue and green light, respectively, to pass to the corresponding photomultiplier. Examination of FIG. 4 shows that the spectrum recorded at photomultiplier PM1 is homodyne and that the spectrum recorded at photomultiplier PM2 is heterodyne. A simultaneous recording can be carried out for example using a spectrum analyser $AS_2$ with two channels, such as the model HP3582A analyzer manufactured by Hewlett Packard. Since this analyser functions within the audio range, it remains necessary to use a Bragg cell (or a diffracting grating) as discussed hereinabove in order to study the hererodyne spectrum.

In that case, the photomultiplier PM1 recording the homodyne spectrum is not necessarily located in the focused beam $F_G$. Finally it will be noted that if spectrum analysers adapted respectively to homodyne and heterodyne ranges are utilized, the use of the Bragg cell is not necessary, but such a solution remains costly.

It should also be noted that the expression of the formulae (1) and (1') hereinabove for the spectra is simplified, but the experimental measurements remain the same, allowing the invention to be applied in a general way.

I claim:

1. A method for obtaining simultaneous velocity and diameter measurements relating to submicronic particles in a state of flow in a fluid comprising the steps of:

producing first and second parallel beams of coherent light from the same laser beam, focusing said parallel beams in a measuring zone through which the fluid passes, initially blocking the passage of said first parallel beam to said measurement zone, detecting at a first solid angle of detection the diffused light issuing from said measurement zone, and spectrally analyzing the detected light over a first frequency range to produce a homodyne spectrum, and, in response to a predetermined critical frequency, unblocking said first parallel beam, detecting at a second solid angle of detection both the diffused light from said second beam and the light from said first beam issuing from said measurement zone, and spectrally analyzing the detected light over a second frequency range to produce a heterodyne spectrum.

2. The method of claim 1 wherein said first solid angle is larger than said second solid angle, said critical frequency and said second frequency range are higher than the highest frequency of said homodyne spectrum and said first frequency range, respectively, and said spectral analysis is conducted with a continuous frequency sweep.

3. The method according to claim 1 or 2 comprising the further step of, when the heterodyne spectrum is produced, one of said parallel beams is shifted by a frequency $f_B$ so as to center the recorded spectrum on the frequency $f_O = f_B - f_{D,B}$, wherein $f_{D,B}$ denotes the Doppler frequency.

4. The method according to claim 3 comprising the further step of reducing the broadening $f_D$ of the spectrum by changing the focusing in response to said critical frequency of said parallel beams.

5. Apparatus for obtaining measurements relating to the velocities, velocity fluctuations and/or diameter of submicronic particles comprising:
a laser light source for producing a laser beam;
a beam splitter for separating said laser beam into first and second parallel beams;
means for focusing said first and second beams in a measurement zone in which the particles are located;
controllable light barrier means for selectively blocking passage of said first beam to said measurement zone;
light detector means for detecting diffused light from said second beam and light from said first beam issuing from said measurement zone;
controllable aperture-defining means for regulating the detection angle of said light detector means;
spectrum analyzer means for spectrally analyzing the light detected by said detecting means for at least one frequency range;
means responsive to the frequency at which said spectrum analyzer is operating for controlling said light barrier means and said aperture-defining means such that said first beam is blocked, said light detector means detects at a first detection angle and said spectrum analyzer means produces a homodyne spectrum for a first frequency range; and such that said first beam is not blocked, said light detector means detects at a second detection angle and said spectrum analyzer means produces a heterodyne spectrum for a second frequency range.

6. The apparatus of claim 5 wherein said light detector means is fixedly disposed in the path defined by said first beam extending from said measurement zone.

7. The apparatus of claim 6 wherein a mask, an opaque screen, or a curtain-diaphragm which is responsive to electronic control constitutes said light barrier means, said light detector means comprises a photomultiplier and a convergent lens disposed in front of said photo detector; said aperture-defining means comprises an adjustable diaphragm responsive to electronic control; said first detection angle is larger than said second detection angle; said control means is responsive to a predetermined critical frequency higher than the highest frequency of said first frequency range; and said apparatus further comprises a neutral filter disposed in the path of said first beam.

8. The apparatus of claim 15 or 16 further comprising means for converting the Doppler frequency $f_{D,B}$ of the detected diffused light to the scale of said spectrum analyzer means.

9. The apparatus of claim 8, further comprising a Bragg cell disposed in the path of said first beam in front of said focusing means.

10. The apparatus of claim 5 or 7 wherein said focusing means comprises means responsive to said control means for varying the angle between the focused first and second beams for the production of each of said homodyne and heterodyne spectra.

11. The apparatus of claim 10 wherein said focusing means comprises a focusing lens, and said angle varying means comprises means for changing said focusing lens.

12. Apparatus comprising a multi-line laser source for producing a laser beam, a beam separator for splitting the laser beam into first and second parallel beams, means for focussing said first and second beams in a measurement zone in which a fluid in a state of flow is located, filter means disposed in the path of said first beam for allowing only light of a first color to pass,
first means for detecting light issuing from said measurement zone, said first detecting means being disposed in the light path of said first beam and including filter means for allowing only light of a second color to be detected;
second means for detecting light issuing from said measurement zone, said second detecting means being disposed in the light path of said second beam and including filter means for allowing only light of said first color to be detected; and
spectrum analyzer means for simultaneously producing homodyne and heterodyne spectra, respectively, from the light detected by said first and second detecting means.

* * * * *